United States Patent [19]

Gawin et al.

[11] Patent Number: 5,468,749
[45] Date of Patent: Nov. 21, 1995

[54] METHOD FOR TREATMENT OF SUBSTANCE ADDICTION

[76] Inventors: Frank H. Gawin, 35 Cottage St.; Robert Byck, 197 McKinley Ave., both of New Haven, Conn. 06511; Marc Alderdice, 94 Logwood Dr., Evansville, Ind. 47710; Jeffrey Schwimmer, 8219 Petersburg Rd., Evansville, Ind. 47711

[21] Appl. No.: 367,823

[22] Filed: Jun. 16, 1989

Related U.S. Application Data

[63] Continuation-in-part of Ser. No. 238,440, Aug. 30, 1988, abandoned.

[51] Int. Cl.$^6$ .................... A61K 31/50; A61K 31/495
[52] U.S. Cl. .................... 514/252; 514/255; 514/813
[58] Field of Search .................... 514/252, 255, 514/813

[56] References Cited

U.S. PATENT DOCUMENTS

| | | | |
|---|---|---|---|
| 3,717,634 | 2/1973 | Wu et al. | 514/252 |
| 3,976,776 | 8/1976 | Wu et al. | 514/252 |
| 4,182,763 | 1/1980 | Casten et al. | 514/252 |
| 4,438,119 | 3/1984 | Allen et al. | 514/252 |
| 4,634,703 | 1/1987 | Kurtz et al. | 514/252 |
| 4,640,921 | 2/1987 | Othmer et al. | 514/252 |
| 4,687,772 | 8/1987 | Alderdice | 514/252 |
| 4,777,173 | 10/1988 | Shrotryia et al. | 514/252 |
| 4,788,189 | 11/1988 | Glazer | 514/252 |
| 4,800,204 | 1/1989 | Mueller | 514/813 |
| 4,871,738 | 10/1989 | Opitz et al. | 514/252 |

FOREIGN PATENT DOCUMENTS

314984A2  5/1989  Germany.

OTHER PUBLICATIONS

Klaus Opitz and Marie—Luise Weischer, Volitional Oral Intake of Nicotine in Tupaias: Drug–Induced Alterations, *Drug and Alcohol Dependence*, vol. 21, pp. 99–104 (1988).
Wu et al., *J. Med. Chem.*, 15, 477 (1972) (2/1).
Allen, et al., *Arzn. Forsch.*, 24/6, 917–922 (1974) (2/4).
Sathanathan, et al., *Curr. Therap. Research*, 18/5; 701–705 (1975) (2/6).
Giannini, et al., *J. Clin Pharmacol.*, 27, 705 (1987).

*Primary Examiner*—Ronald W. Griffin

[57] ABSTRACT

Certain azapirone compounds and their pharmaceutically acceptable salts are useful in the treatment of substance addiction.

16 Claims, No Drawings

METHOD FOR TREATMENT OF SUBSTANCE ADDICTION

CROSS REFERENCE TO RELATED APPLICATION

This is a continuation-in-part application of Ser. No. 238,440 filed Aug. 30, 1988, now abandoned.

FIELD OF THE INVENTION

This invention is concerned with a drug bioaffecting body-treating process which employs the pyrimidine compound 8-[4-[4-( 2-pyrimidinyl )-1-piperazinyl]butyl]-8-azaspiro-[4.5]decane-7,9-dione or a pharmaceutically acceptable acid addition salt thereof.

BACKGROUND OF THE INVENTION

The pyrimidine compound with which the present invention is concerned has the following structural formula

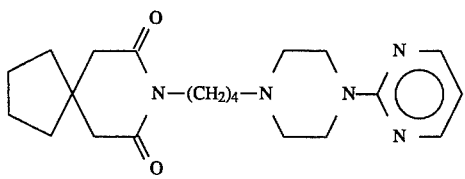

and is known as buspirone. The hydrochloride salt has been referred to in the prior art as MJ 9022-1 and as buspirone hydrochloride. Other acid addition salts thereof are named by combining "buspirone" with the appropriate word to define the acid from which it is prepared as in "buspirone hydrochloride". The latter is the United States Adopted Name (USAN); refer to J. American Med. Assoc. 225, 520 (1973).

The synthesis of the compound and the disclosure of its psychotropic properties are described in the following patents and publications.

1. Y. H. Wu, et al., *J. Med. Chem.*, 15,477 (1972).
2. Y. H. Wu, et al., U.S. Pat. No. 3,717,634 which issued Feb. 20, 1973.
3. L. E. Allen et al., Arzneium. Forsch., 24, No. 6, 917–922 (1974).
4. G. L. Sathananthan, et al., *Current Therapeutic Research*, 18/5, 701–705 (1975).
5. Y. H. Wu, et al., U.S. Pat. No. 3,976,776, issued Aug. 24, 1976.

The following patent references disclose and claim additional uses which relate to buspirone's pharmacological effects on the central nervous system.

6. The use of buspirone hydrochloride as a novel antianxiety agent for the treatment of neurotic patients is described in G. P. Casten, et al., U.S. Pat. No. 4,182,763, issued Jan. 9, 1980.
7. Allen, et al., disclose the use of buspirone in treating extrapyramidal motor disorders in U.S. Pat. No. 4,438, 119, issued Mar. 20, 1984.
8. Buspirone's use in sexual dysfunction was described by Othmer, et al., in U.S. Pat. No. 4,640,921, issued Feb. 3, 1987.
9. Kurtz, et al., in U.S. Pat. No. 4,634,703, issued Jan. 6, 1987 disclose buspirone's use in treating panic disorders.
10. Alderdice discloses the use of buspirone in the improvement of short term memory in U.S. Pat. No. 4,687, 772, issued Aug. 18, 1987.
11. U.S. patent application Ser. No. 030,659 of Shrotriya and Casten, filed Mar. 25, 1987 discloses and claims the use of buspirone in treating alcohol abuse.

None of the above-referenced uses of buspirone, separately or in joint, would teach or suggest the use of the present invention, a method for treatment of substance addiction. While alcohol is often included in listings of abused and/or addicting substances, nonetheless it would not be obvious beforehand that an agent useful in treating alcohol abuse would also find use in treating the addiction to such diverse substances as tobacco, marijuana, amphetamines, cocaine and heroin as well as treating eating disorders. Although alcoholics often abuse other substances as well as alcohol, again it would not be obvious beforehand that buspirone would be useful in treating abuse and addiction to these other addicting substances.

In summary, there exists nothing in the prior art, including the specific references set forth hereinabove, which would make obvious the use of buspirone to treat substance addiction.

SUMMARY OF THE INVENTION

The method of the present invention is intended for the treatment of addiction to substances such as tobacco, marijuana, cocaine, opiates, methadone, crack, PCP, and amphetamines as well as treating eating disorders in patients exhibiting these addictions or disorders. The method essentially involves administration of buspirone, or a pharmacologically acceptable acid addition salt thereof, to a patient in need of such treatment. For use in the instant method oral administration of buspirone hydrochloride from about 10 to 80 mg per day in divided doses is anticipated as being the preferred dosage regimen.

DETAILED DESCRIPTION OF THE INVENTION

This invention results from the discovery that buspirone administration is an effective treatment in assisting patients in their effort to halt abuse of and/or overcome addiction to abused and/or addictive substances. In the context of this invention, substance addiction comprises over-eating and the habitual use of substances such as tobacco, marijuana, cocaine, opiates, methadone, amphetamines, methylphenidate, and other substances of an addicting nature.

"Overeating" is intended to comprise not only frank overeating habits such as food-hinging and carbohydrate craving but also encompasses eating disorders such as bulimia and anorexia nervosa. "Substances" refers to but is not limited to tobacco (nicotine), marijuana (THC), cocaine, opiates (morphine, heroin, etc.), methadone, crack, PCP (phencyclidine, angel dust), amphetamines, methylphenidate and related designer drugs.

The term "use" is intended to encompass all forms of administration of these substances to the body but most commonly refers to the more widely practiced forms of presentation of these substances, e.g. smoking tobacco and marijuana, nasal inhalation of cocaine and certain of its derivatives, intravenous injection of opiates, etc. The classification of these substances, their mode of abuse, and pharmacologic consequences are well known to those familiar with dealing with patients suffering from substance addiction.

Certain components of buspirone's pharmacology, particularly its interaction with monoaminergic pathways in discrete brain areas, provide a rationale for the role of buspirone in antagonizing substance addiction in general. Continued over-indulgence or inappropriate consumption of foods as well as habitual use of other addictive substances, relies in part on "craving". In subjects suffering from substance addictions, "craving" is more of a demand, rather than a desire, for the addictive substance. Buspirone's interactions with monoaminergic transmission in brain regions associated with pleasure, reward, and appetite appears to result in reducing craving. This effect of buspirone on pleasure regions of brain is evidenced by a component of mild dysphoria in its pharmacologic profile.

There are two aspects to the use of buspirone in treating substance addiction. One aspect is that buspirone effects actual reduction in both craving for and consumption of the abused and/or addicting substance. The second aspect is that buspirone alleviates the symptomatology associated with the withdrawal process itself.

Reduction of craving, as effected by buspirone, makes it useful in treatment of substance addiction, either as a single agent or as adjunct therapy in addition to counseling, appetite suppressants, nicotine substitution, methadone treatment, etc. Additionally, buspirone alleviates other characteristic symptoms associated with withdrawal from an addictive substance. These symptoms comprise anxiety, depression., fatigue, malaise, anhedonia, irritability, anger and hostility.

Clinical experience with buspirone, as well as consideration of the chronic nature of addictive disorders, would indicate that the beneficial effects of buspirone treatment may require a period of chronic administration, usually on the order of two to four weeks, prior to their full appearance. It is appreciated by those skilled in the art that the time to emergence of full therapeutic response, as well as the dosage levels required, can vary from patient to patient.

An additional advantage for buspirone treatment of substance addiction is that its inhibitory effects on overeating can act to limit the common occurrence of a large increase in food intake during a drug or smoking withdrawal period which usually leads to unwanted gains in body weight.

Buspirone's effectiveness in treating eating disorders, over-eating, tobacco and marijuana smoking, and addictive drug use has been confirmed by results of clinical treatment of patients suffering from these disorders and addictions. Most of the patients treated with buspirone had demonstrated a lack of response to other treatments attempted for these disorders and substance addictions. It is recognized that there are no universally effective treatments for substance addiction.

As an example of buspirone's use in substance addiction, perhaps the most common addiction in terms of population is tobacco smoking, for which there is no widely accepted treatment for effecting smoking reduction or cessation. In a pilot study of eight smokers who had used over one and one-half packs of cigarettes daily for over five years and had had no success in previous attempts to stop smoking, buspirone treatment was employed. None of the patients was suffering from an anxiety disorder. Buspirone was administered for six weeks beginning with 15 to 30 mg buspirone per day given in divided doses and the dose increased by 10 mg increments to 60–100mg/day. One patient dropped out of the study after week three but the remaining seven patients completed the study reporting sustained reduction in their urge to smoke. Buspirone effects on the urge to smoke appeared during the second to fourth week of the study and resulted in reducing the effort required to cease smoking to a level lower than ever experienced in all previous cessation attempts. No adjunctive psychological intervention was employed in this study. Every subject decreased smoking to seven or less cigarettes per day for at least a one week period (defined as a substantially reduced smoking period). "Craving" or desire to smoke was monitored over the course of the study by means of a 20 point analog scale. When smokers attempt to reduce their smoking habit, craving usually increases. In this study, craving was significantly reduced from the pretreatment level as the study progressed and was less than 30% of the pretreatment level at the end of the first week of substantially reduced smoking (average of $\leq$ seven cigarettes per day). Although only about half of the patients completely ceased smoking, the ultimate goal for antismoking treatment, nonetheless the remaining patients exhibited substantial reduction in their smoking habit which also yields health benefits.

Buspirone was also studied by incorporating its administration in a clinical weight reduction program. Patients of both sexes, with a desire to lose weight were treated with buspirone 15 mg (or greater) p.o., t.i.d. Weight loss effects typically appeared following 3 to 4 weeks of buspirone treatment. The range of weight loss reported was on the order of 5 to 40 lbs per patient. Follow-up of the patients indicated that the weight loss was sustained and was not the short term loss commonly seen with many weight reduction programs in which the patient regains the weight in a short period of time following program cessation.

Another effect of buspirone treatment on smokers and other patients with substance addictions and eating disorders was relief of withdrawal symptoms commonly associated with cessation or reduction in consumption of the addictive substance. Buspirone appears to be unique in reducing not only the anxiety, depression, malaise, anhedonia, anger, hostility, irritability, frustration and fatigue associated with the withdrawal process but in also reducing the actual craving for the substance.

This two-pronged action of buspirone makes it especially useful in the more serious addictions such as opiates comprising morphine, heroin and the substitution drug methadone.

In summary, the present invention concerns a method for treating substance addiction which comprises eating disorders and habitual use of tobacco, marijuana, cocaine, opiates and other substances. The method of treatment involves administration of buspirone, or one of its pharmaceutically acceptable salts, in the form of a pharmaceutical composition, either alone or as an adjunct to their therapies.

Pharmaceutically acceptable acid addition salts of buspirone and methods of pharmaceutical formulation are described in the patents of Wu, et al., U.S. Pat. Nos. 3,717,634 and 3,976,776 which are incorporated in their entirety herein be referenced.

Administration of buspirone according to the present invention may be made by the parenteral, oral or rectal routes. Parenteral administration comprises injection, e.g. intravenous or intramuscular injection, as well as any other parenteral route of administration. The oral route is preferred, however; the clinical dosage range for alleviation of substance addiction is expected to be somewhat higher compared with that routinely employed for anti-anxiety usage, but can vary to some extent. In general, the expected amount of buspirone administered would be less than about 100 mg per day, generally in the 20 mg to 80 mg range, and preferably in the range of 30–60 mg per day. Since the dosage should be tailored to the individual patient, the usual practice is to commence with a dose of about 5 mg administered two or three or more times per day and then to increase the dose every two to three days by 5 mg at each dosage time until the desired response is observed or until the patient exhibits side effects. Single daily dosage may be applicable in some instances. The main side-effect experienced by patients being treated for substance addiction was dizziness.

FURTHER DETAILED DESCRIPTION

Additional study indicates that other members of the general "azapirone" structural class of psychotropic agents may also be employed in the method of the present invention. These related compounds display similar pharmacological actions relating to interaction with monoaminergic pathways in particular areas of brain. Specifically, functional binding of these agents at monoaminergic receptor sites in brain indicate a neuropharmacologic profile which would render these azapirone relatives useful in treating substance addiction. Accumulating clinical results also provide additional support for use of other azapirones in addition to buspirone as treatments for substance addiction.

To this point in time, there has been no disclosure of the use of additional azapirone compounds for treating substance abuse. Buspirone, gepirone and ipsapirone have been disclosed as being useful in treating alcoholism; cf: European patent application 303,951A2 published February, 1989.

The method of the present invention then is being broadened to encompass the use of related azapirone compounds of Formula I.

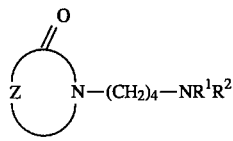
                                                    I

In Formula I, Z is a member selected from the group

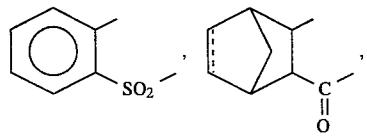

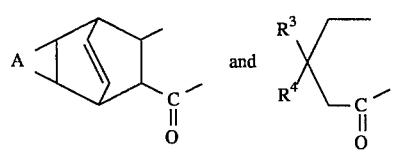

with $R^3$ and $R^4$ being independently selected from $C_{1-4}$ alkyl and hydrogen or $R^3$ and $R^4$ can be taken together as a butanediyl or pentanediyl chain thereby forming a spiro ring system. $R^1$ and $R^2$ in Formula I are either taken together

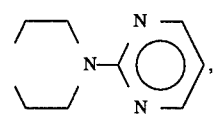

as thereby forming a pyrimidinylpiperazine moiety or $R^1$ is hydrogen and $R^2$ is the group

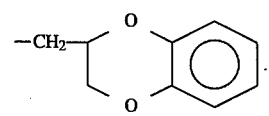

A can be $-CH_2-$, $-O-$, $-CH_2CH_2-$ or $-CH=CH-$. The dotted and solid line represents either a single or a double chemical bond.

Preferred azapirones are the following compounds, listed below in Table 1, which have been disclosed previously as psychotropic agents with useful anxiolytic properties.

Administration of these azapirones for use in the method of the present invention is to be done in the same manner as for buspirone as outlined supra. Consistent with good clinical practice, some dose adjustments may be employed in the prescribing of the treatment for individual patients and such dose adjustment is known to one skilled in the medical arts.

TABLE 1

Specific Azapirone Compounds

| STRUCTURE | REFERENCE |
|---|---|
| BUSPIRONE | U.S. Pat. No. 3,717,634 |

TABLE 1-continued
Specific Azapirone Compounds

| STRUCTURE | REFERENCE |
|---|---|
| GEPIRONE | U.S. Pat. No. 4,423,049 |
| IPSAPIRONE | EP 129,128A |
| SM-3997 | U.S. Pat. No. 4,507,303 |
| WY-47,846 | J. Med. Chem., 1988 31, 1382–1392 |
| MDL 72832 | U.S. Pat. No. 4,612,312 |

What is claimed is:

1. A method for treatment of substance addiction, the substance addiction comprising the habitual use of tobacco, the method comprising administration of a therapeutically effective regimen of a Formula I azapirone compound or a pharmaceutically effective acid addition salt thereof to a patient in need of such treatment;

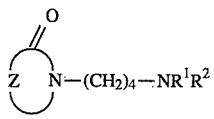

I wherein
Z is a member selected from the group consisting of

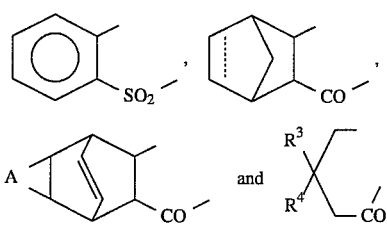

with the dotted and solid line representing either a single or a double chemical bond; A being selected from the group consisting of O, $CH_2$, $CH_2CH_2$ and CH=CH;

$R^3$ and $R^4$ being independently selected from hydrogen and $C_{1-4}$ alkyl or $R^3$ and $R^4$ can be taken together as a butanediyl or pentanediyl chain; and $R^1$ and $R^2$ are either taken together as

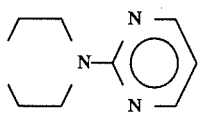

or R¹ is hydrogen and R² is

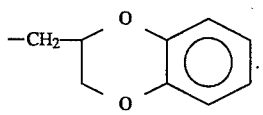

2. The method of claim 1 wherein Z in the Formula I compound is

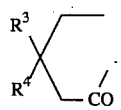

3. The method of claim 1 wherein Z in the Formula I compound is

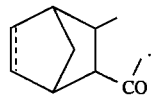

4. The method of claim 1 wherein Z in the Formula I compound is

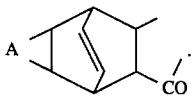

5. The method of claim 1 wherein NR¹R² is

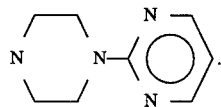

6. The method of claim 1 wherein the Formula I compound is buspirone.

7. The method of claim 1 wherein the Formula I compound is gepirone.

8. The method of claim 1 wherein the Formula I compound is ipsapirone.

9. The method of claim 1 wherein the Formula I compound is SM 3997.

10. The method of claim 1 wherein the Formula I compound is WY 47846.

11. The method of claim 1 wherein the Formula I compound is MDL 72832.

12. The method of claim 1 wherein buspirone hydrochloride is employed and dosage is by the oral route.

13. The method of claim 12 wherein a daily dose of about 10 to 80 mg is employed.

14. The method of claim 12 wherein said daily dose is divided and administered b.i.d.

15. The method of claim 12 wherein said daily dose is divided and administered t.i.d.

16. A method for treatment of habitual use of tobacco addiction;

the method comprising administration of a therapeutically effective regimen of a Formula I azapirone compound or a pharmaceutically effective acid addition salt thereof to a patient in need of such treatment;

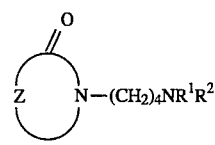

wherein
Z is a member selected from the group consisting of

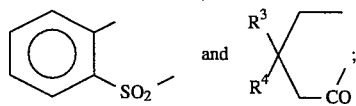

R³ and R⁴ each being methyl or R³ and R⁴ can be taken together as a butanediyl chain; and R¹ and R² are taken together as

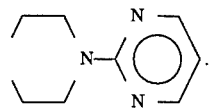

* * * * *